US006929908B1

(12) United States Patent
De Rodriguez et al.

(10) Patent No.: US 6,929,908 B1
(45) Date of Patent: Aug. 16, 2005

(54) METHOD OF PROCESSING BLOOD SAMPLES IN ORDER TO PRODUCE DNA COMPLEX PATTERNS FOR DIAGNOSTIC APPLICATIONS

(75) Inventors: Gloria Elena Loen Paz De Rodriguez, San Jose, CA (US); Gin Wu, San Jose, CA (US)

(73) Assignee: Opto Genetics, Inc., San Jose, CA (US)

( * ) Notice: Subject to any disclaimer, the term of this patent is extended or adjusted under 35 U.S.C. 154(b) by 558 days.

(21) Appl. No.: 09/764,783

(22) Filed: Jan. 17, 2001

(51) Int. Cl.[7] .......................... C12Q 1/68; G01N 31/00

(52) U.S. Cl. ................ 435/6; 436/17; 436/18

(58) Field of Search .................... 424/133.1, 138.1, 424/6; 435/172.2, 328, 344, 6; 530/387.3, 530/387.7, 388.8; 436/17, 18, 63, 65

(56) References Cited

OTHER PUBLICATIONS

Celis, J. E., "Cell Biology, A Laboratory Handbook, vol. 2", 1994; Academic Press Inc., San Diego, CA. See p. 5, paragraph 4-p. 6, paragraph 1, See p. 446, paragraph-p. 447, paragraph.

Stryer, L., "Biochemistry" 3rd Edition; 1988; W.H. Freedman and Company, New York See p. 5, paragraph 2 See p. 80, paragraph 1 See p. 83, paragraphs 2-4 Figures 1.5, 4.18, 4.19.

Henderson, E., "Imaging and nanodissection of individual supercoiled plasmids by atomic force microscopy", Nucleic Acids Research, vol. 20, No. 3; 1992. pp. 445-447 See abstract See p. 445, paragraph 1: Figure 1C.

Sambrook, J. et al., Molecular Cloning, A Laboratory Manual, vol. 3; 1989, Cold Spring Harbour Laboratory Press, Cold Spring Harbour. See p. E.3, paragraph 1-p. E.4, paragraph 4.

*Primary Examiner*—Jehanne Sitton
(74) *Attorney, Agent, or Firm*—Law Offices of Royal W. Craig

(57) ABSTRACT

A method for processing blood samples in order to produce DNA complex patterns for diagnostic applications.

6 Claims, 6 Drawing Sheets

FIG. 2A
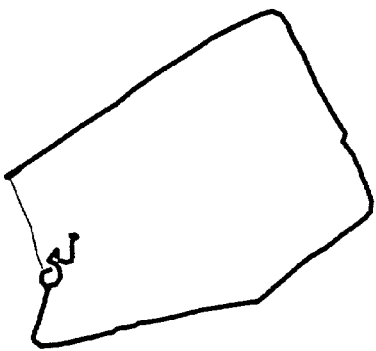
FIG. 2B
FIG. 2C
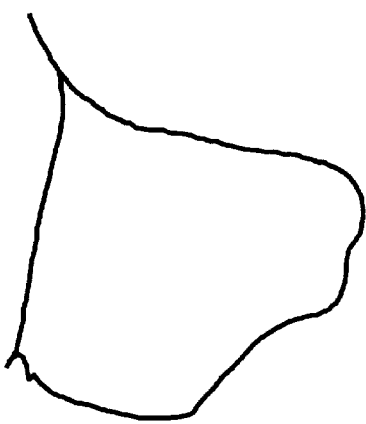
FIG. 2D

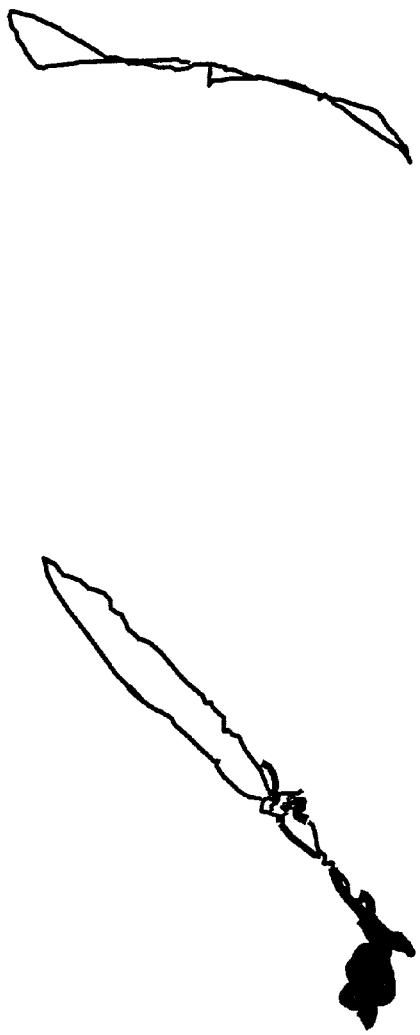
FIG. 3A
FIG. 3B
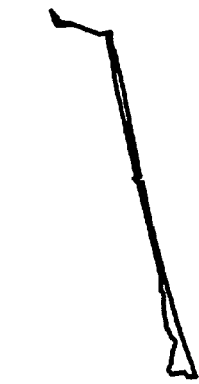
FIG. 3D
FIG. 3C

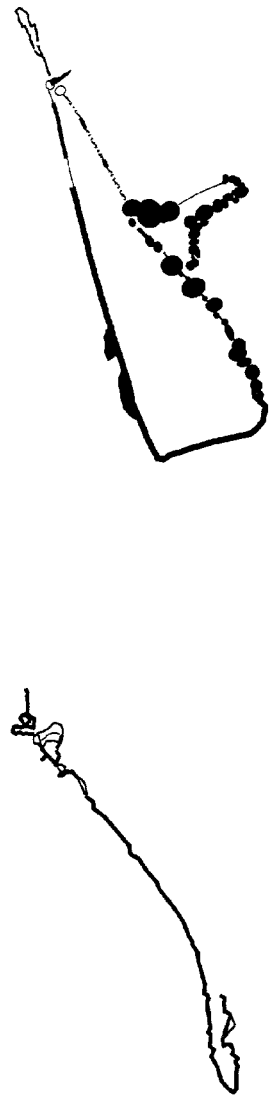
FIG. 4
FIG. 5
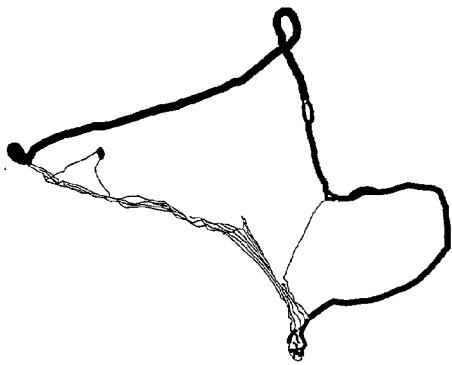
FIG. 6

METHOD OF PROCESSING BLOOD SAMPLES IN ORDER TO PRODUCE DNA COMPLEX PATTERNS FOR DIAGNOSTIC APPLICATIONS

FIELD OF INVENTION

This invention relates to the field of medical diagnostic techniques, and more specifically to the processing and preparation of blood samples to produce precipitated samples with unique and identifiable patterns.

BACKGROUND OF INVENTION

Traditional disease diagnosis normally begins with a physical examination of the patient's symptoms and a review of the patient's medical and family histories. The diagnosis is usually confirmed as the patient's disease progresses and additional symptoms appear. A proper diagnosis may often times require that laboratory tests be performed in order to provide more detailed information about the patient's condition. In this regard, there are numerous specific tests for different diseases that have been developed and used in modern medicine. Some of the most common tests involve obtaining a blood sample from a patient and examining the sample in the laboratory for both the general and specific diagnostic purposes. Since the circulation of blood is the most significant biochemical transporting and exchanging system in the human body, most illnesses will produce or induce certain changes in the blood's content or its properties. It does not matter whether the human body is exposed to a toxin released from a pathogen or from a pathogen-induced immune response, or whether the body is under the influence of an endocrine system dysfunction or is experiencing nutritional or metabolic problems, all of these abnormal conditions have the potential to induce significant changes in the blood. Therefore, blood samples have become the most commonly collected samples for the laboratory diagnosis and forensic evidence.

Macroscopically, the composition of blood is categorized into two major components: the cellular portion consisting of blood cells, and the fluid portion called plasma. Normally, a blood sample will start to coagulate after being extracted from a blood vessel. The coagulation process involves the aggregation of the blood cells to form a dark solid precipitation. The remaining liquid portion of the blood is called serum. If the blood sample is mixed with an anti-coagulant during or immediately after collection, the blood will not coagulate and will stay in fluid form. If the anti-coagulated blood is centrifuged or kept in a stationary state for a period of time, the blood cells will precipitate. The up-liquid portion of the anti-coagulated blood is the plasma. Depending on the test being conducted, the blood samples are normally collected and used in these three forms: the whole blood, plasma or serum. Most laboratory tests, however, focus on the serum component of coagulated blood.

There are many prior art technologies for detecting changes in blood components and relating the changes as a diagnostic tool to indicate the presence of different diseases. For example, an increase in a patient's white blood cell count generally indicates an inflammation occurring somewhere in the body. A low level hemoglobin number indicates anemia. Without proper medication, diabetes patients will show an abnormal blood glucose level. Therefore, the changes of the blood components are not only resulting from the changes of blood system itself but also can reflect many diseases on other parts of the body. Literally, hundreds of blood components have been identified and used to assist in diagnosing disease. There are still a significant portion of components and functions yet being identified. In this regard, the molecular changes of well-defined markers in the blood are readily detected for many well defined and understood diseases. Most of infectious diseases that induce the immune responses are easily identified by the detection of antibodies in the blood. Unfortunately, for many not well defined physiological illnesses, there are no apparent changes in the body, nor in the blood, until the relatively late stages of the disease. Especially for many kinds of cancer, there is no good marker available.

Genes were originally understood to be the basic molecular unit which controlled inheritance. After the development of the advanced biochemical technology, the chemical structural unit of genes has been revealed to be nucleic acids. Except for a small number of RNA (ribonucleic acid) viruses, genes in all other living organisms are formed from DNA (deoxyribonucleic acid). DNA strands are extremely long and unbranched nucleic acid polymers that contain many different genes in each strand. In living cells, DNA strands fold tightly with certain proteins to form a compact nucleoprotein complex called chromatin. Normally, DNA strands in this form are not active. These sequestered genes can be activated, however, as a result of certain controlled mechanisms that are, in general, not well understood by today's science. Though some studies on the physical structure of the DNA double helix were done in the early stages of DNA analysis by biochemists, biochemistry and molecular biology research done today on the structure and functionality of DNA are mostly confined to an analysis of DNA after it has been almost completely isolated from its nucleoprotein complex.

During the later development stage of molecular biology, the identification of Enhancers, a kind of gene expression regulator, and the discovery of ribozymes have indicated that an analysis of the secondary or tertiary structure of entire nucleic acid complex, beyond just the linear sequence of the nucleic acid units, might have a potentially more important role in the analysis and understanding of gene regulation. The gene rearrangement process in the immune system also has indicated that gene regulation is involved in changes in substantial portions of DNA, instead of just an alteration of a few nucleic acids that only affected a very small portion of entire DNA sequence. Unfortunately, however, due to the extremely long and thin structure of DNA and its dense and compact nucleoprotein complex, it is extremely difficult to isolate the DNA without significantly altering its nucleoprotein complex. Therefore, there is not much known about the structural changes of the nucleoprotein complex. As a result, there is presently no diagnostic tool available which can detect changes in DNA and its associated nucleoprotein complex.

It is well known that white blood cells are responsible for the body's defense system. It is also known that, based upon immunology studies, normal immune response requires about seven (7) days before any specific antibody production clone of a B-lymphocyte can be detected. This fact indicates that the activation of those specific clones of antibody production B-lymphocytes started much earlier, which indicates that the cells responsible for cellular immunity also must have been activated earlier. Unfortunately, these early and delicate changes inside the immunocytes are well below the detectable level of current technology.

SUMMARY OF THE INVENTION

In order to overcome the technological barrier, the present invention provides a new and unique method that isolates and preserves the structural integrity of DNA and its associated nucleoprotein complex ("DNA complex"). The method includes the aggregation and deposition of the DNA complex from the blood of a human being in order to form a unique pattern which can be used as a medical diagnostic tool to identify a change in the body caused by a specific physiological or pathological condition. The method identifies a change in the body by comparing the pattern of a person before being exposed to a specific physiological or pathological condition to the pattern of a person after being exposed to the condition. The specific condition causing the change is determined by identifying and associating the unique pattern to the specific condition or disease. Another important aspect of the present invention is the ability to detect changes in the body during the early stages of the physiological or pathological condition. The present invention can be used as a diagnostic tool to aid in the determination of, among other things, the sex of a human fetus within a few days after conception, and the presence of a cancerous condition in the earliest stage of the disease.

Before the method of the present invention was discovered, standard DNA extraction procedures used in molecular biology research cause severe damage to the integrity of the DNA complex. These procedures strip off all of the DNA's associated proteins and related components in order to isolate the DNA. Unfortunately, all of the DNA complex's structure is demolished leaving DNA in an isolated and an approximately linear and uniform form. As a result, it is not possible on a macroscopic level to ascertain any structural difference between normal and altered DNA. The present invention has overcome this problem in order to enable researchers to distinguish normal DNA from altered DNA by providing them with a method to compare the patterns associated with a normal DNA complex to the patterns associated with an abnormal DNA complex.

BRIEF DESCRIPTION OF THE DRAWINGS

The present invention is further described by reference to the following drawings:

FIG. 2A is a diagram of the pattern formed using the present invention to process the blood from a pregnant woman carrying a female fetus for six (6) weeks.

FIG. 2B is a diagram of the pattern formed using the present invention to process the blood from a pregnant woman carrying a female fetus for seven (7) weeks.

FIG. 2C is a diagram of the pattern formed using the present invention to process the blood from a pregnant woman carrying a female fetus for eight (8) weeks.

FIG. 2D is a diagram of the pattern formed using the present invention to process the blood from a pregnant woman carrying a female fetus for nine (9) weeks.

FIG. 3A is a diagram of the pattern formed using the present invention to process the blood from a pregnant woman carrying a male fetus for five (5) weeks.

FIG. 3B is a diagram of the pattern formed using the present invention to process the blood from a pregnant woman carrying a male fetus for seven (7) weeks.

FIG. 3C is a diagram of the pattern formed using the present invention to process the blood from a pregnant woman carrying a male fetus for nine (9) weeks.

FIG. 3D is a diagram of the pattern formed using the present invention to process the blood from a pregnant woman carrying a male fetus for ten (10) weeks.

FIG. 4 is a diagram of the pattern formed using the present invention to process the blood of a healthy woman.

FIG. 5 is a diagram of the pattern formed using the present invention to process the blood of a woman with breast cancer.

FIG. 6 is a diagram of the pattern formed using the present invention to process the blood of a woman with cervical cancer.

DETAILED DESCRIPTION OF THE INVENTION

Figure 1:
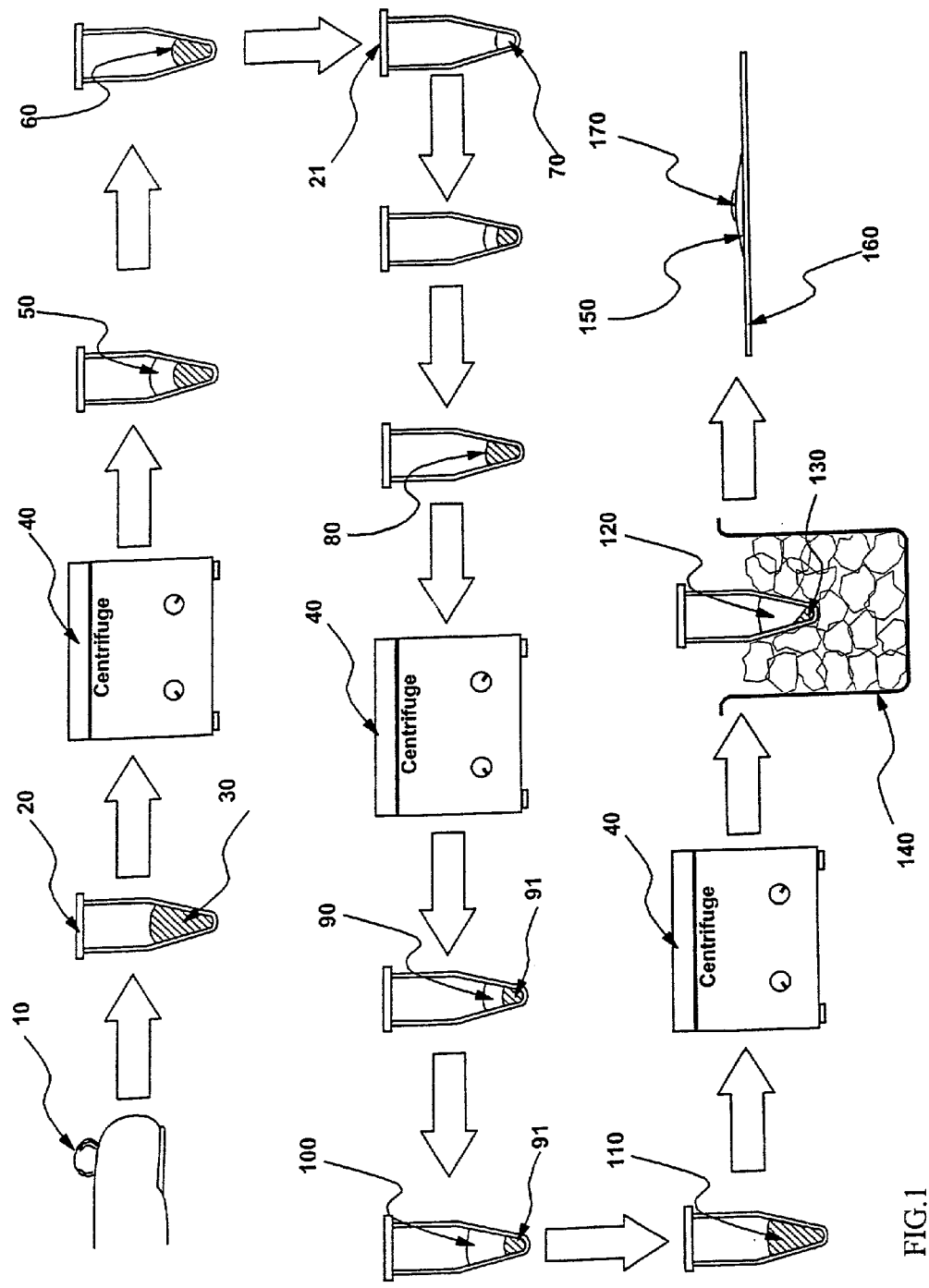
FIG. 1 is a diagrammatical illustration of the present invention's method of processing human blood samples.

The new and unique method of the present invention, which is the result of extensive experimentation, is illustrated diagrammatically in FIG. 1. Initially, fresh human blood 10 is collected and placed in a first centrifuge tube 20, where it is mixed with an anticoagulant to form an anticoagulated blood mixture 30. The centrifuge tube 20 containing the anticoagulated blood mixture 30 is then placed in a centrifuge 40. Centrifugation causes the anticoagulated blood to separate into a top portion, containing blood plasma 50, which is removed and discarded, leaving behind blood cells 60 in centrifuge tube 20.

In a second centrifuge tube 21, a blood cell solution is prepared in accordance with the following steps: first, approximately two (2) volumes of Tris-buffer is placed into the centrifuge tube 21; second, approximately one (1) volume of Tris-buffer saturated phenol, prepared by mixing re-distilled phenol with Tris-buffer, is added to centrifuge tube 21; and lastly, approximately four (4) volumes of the blood cells 60 are added to centrifuge tube 21. In each of the first two steps, the Tris-buffer consists of 0.5 M Tris, 0.2 M EDTA, 0.6% NaCl, having a pH of between 10.3 and 10.4. The blood cell solution is then mixed well in the centrifuge tube 21 to form a first blood cell mixture 80, and said mixture 80 is placed in the centrifuge 40 where the mixture is centrifuged at 11,000 rpm for approximately 10 minutes to produce a first liquid phase 90 and first blood cell debris 91. Next, a phenol/chloroform solution 100, consisting of approximately one (1) volume of Tris-buffer saturated phenol, prepared as described above, and approximately one (1) volume of chloroform, is added to the centrifuge tube 21 containing the first liquid phase 90 and first blood cell debris 91. The contents in centrifuge tube 21 are then mixed well to produce a second blood cell mixture 110.

The centrifuge tube 21 containing the second blood cell mixture 110 is placed in centrifuge 40 and centrifuged at approximately 11,000 rpm for approximately 15 minutes to produce a second liquid phase 120 and second blood cell debris 130. The tube 21 containing the second liquid phase 120 and debris 130 is then placed in a beaker of ice 140 for approximately fifteen (15) minutes. A slide 160 is then prepared by placing an acid alcohol sample 150 consisting of approximately twenty-five (25) volumes of freshly made 20% acid alcohol (i.e., ethanol containing 20% acetic acid)

onto the top surface of the slide 160, and immediately adding a blood cell sample 170 consisting of approximately one (1) volume of the second liquid phase 120, which has been cooled, onto the center portion of the top surface of acid alcohol sample 150. The slide 160 is then maintained on a stable surface in order to allow acid alcohol sample 150 and blood cell sample 170 to dry on the slide at room temperature without any disturbance for 10 to 15 minutes. During the drying phase, the DNA complex contained within blood cell sample 170 aggregates in the acid alcohol sample 150 and deposits a unique pattern on slide 160.

It has been established through extensive experiments that so long as the relative concentrations of blood cells, Tris-buffer diluted phenol, Tris-buffer saturated phenol and chloroform are maintained, the resulting patterns for any given blood sample from the same person will exhibit practically identical characteristics. Visual analysis of the patterns under an optical microscope has revealed that the patterns are useful as a diagnostic tool to assist in the determination of whether a human being has been exposed to a specific physiological or pathological condition.

In one set of experiments, the blood of pregnant women at various stages in their pregnancy was used in accordance with the present invention to produce the patterns. In each instance, the following procedure was utilized. After obtaining whole blood from a woman, the blood was placed in a centrifuge tube where it was mixed with an anti-coagulant to form an anti-coagulated blood mixture. The anti-coagulated blood is then centrifuged and the plasma was removed, leaving the blood cells in the tube. In another centrifuge tube, a blood cell solution was prepared in accordance with the following steps: first, two (2) volumes of Tris-buffer were placed into the centrifuge tube; second, one (1) volume of Tris-buffer saturated phenol, which was prepared by mixing re-distilled phenol with Tris-buffer, was added to the centrifuge tube; and lastly, four (4) volumes of the blood cells were added to the centrifuge tube. In each of the first two steps, the Tris-buffer consisted of 0.5 M Tris, 0.2 M EDTA, 0.6% NaCl, having a pH of between 10.3 and 10.4. The blood cell solution was then mixed well to produce a first blood cell mixture, and the mixture was centrifuged for ten (10) minutes at 11,000 rpm to produce a first liquid phase and a first blood cell debris, which formed as a precipitate in the tube. Next, a phenol/chloroform solution was prepared by mixing 2.5 µl of Tris-buffer saturated phenol, prepared as described above, with 2.5 µl chloroform, and the phenol/chloroform solution was added to the centrifuge tube containing the first liquid phase and first blood cell debris, which was mixed well to produce a second blood cell mixture.

The second blood cell mixture was then centrifuged for fifteen (15) minutes at 11,000 rpm to produce a second liquid phase and second blood cell debris, which formed as a precipitate in the tube. The centrifuge tube containing the second liquid phase and second blood cell debris was then removed from the centrifuge and placed in a beaker of ice for fifteen (15) minutes. A slide was prepared by placing an acid alcohol sample of 25 µl of freshly prepared 20% acid alcohol (i.e., ethanol containing 20% acetic acid) onto the top surface of the slide, and a blood cell sample of 1.0 µl of the cooled second liquid phase was immediately added to the center of the top surface of the acid alcohol sample. The samples were then allowed to dry on the slide at room temperature without any disturbance for 10 to 15 minutes. After the samples had dried, the slide was viewed under an optical microscope.

Figures 2E, 2F:
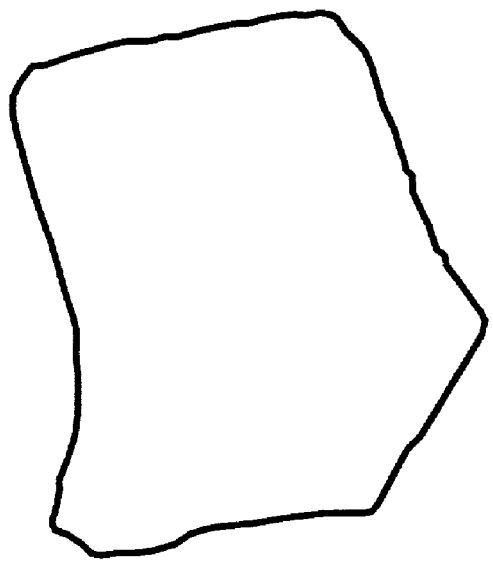
FIG. 2E is a diagram of the pattern formed using the present invention to process the blood from a pregnant woman carrying a female fetus for ten (10) weeks.
FIG. 2F is a diagram of the pattern formed using the present invention to process the blood from a pregnant woman carrying female twins.
Figure 3E:
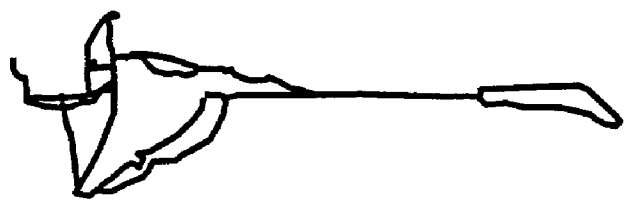
FIG. 3E is a diagram of the pattern formed using the present invention to process the blood from a pregnant woman carrying a male fetus for eleven (11) weeks.

Microscopic analysis of each sample from the blood of the pregnant women participating in the experiment revealed that the patterns that formed on the slide from women carrying a female fetus were readily distinguishable from the patterns formed from women carrying a male fetus. It was also discovered that the patterns were distinguishable in the earliest stages of pregnancy. The pattern diagrams shown in FIGS. 2A through 2F were obtained by using the present invention, as described in the experimental procedure above, to process a blood sample obtained from each of six (6) different pregnant women carrying a female fetus. The gestation period for the women carrying a female fetus was between six (6) and ten (10) weeks. Each of these patterns exhibits a single and approximately circular or polygonal ring shape, with the exception of FIG. 2F which exhibits a double ring shape formed from the blood of one of the women who was carrying twins.

By comparison, the pattern diagrams shown in FIGS. 3A through 3E were formed by using the present invention to process a blood sample obtained from each of five (5) different women carrying a male fetus. The gestation period for the women carrying a male fetus was between five (5) and eleven (11) weeks. Each of these patterns reveals either a generally linear pattern, or a linear pattern in combination with one or more elongated or collapsed ring patterns. None of the patterns illustrated in FIGS. 3A through 3E, however, exhibits the circular or polygonal shapes exhibited by the patterns illustrated in FIGS. 2A through 2F.

In another set of experiments, the present invention was used to produce patterns from the blood of healthy persons, and these patterns were compared to the patterns from women with breast and cervical cancer. FIG. 4 diagrammatically illustrates a typical pattern formed from a healthy woman, and FIG. 5 and FIG. 6 illustrate the patterns of a woman with breast and cervical cancer, respectively.

The pattern from the healthy women, as shown in FIG. 4 displays a generally linear, single continuous strand, and throughout most of the strand's length it is smooth. Although not shown, in other healthy persons the strand forms a nearly circular shape. These smooth strand shapes are readily distinguishable from the irregular beaded and branched strand shapes in women with cancer. The pattern formed from the blood cells of a woman with breast cancer, as illustrated in FIG. 5, reveals a generally polygonal shaped strand that is beaded and there is a substantial discontinuity on one side of the polygonal shaped strand. The discontinuity appears as a branching pattern over from the polygonal shaped strand. In the case of cervical cancer, as shown in FIG. 6, the strand pattern that was formed appears to be generally smooth, but its shape is irregular, being neither linear, circular, nor polygonal, and there is a discontinuity or loop on one portion of the strand, and thinner strands form branches which extend from one end of the thicker strand to the other end and one thin strand extends across the interior of the irregularly shaped strand pattern.

Based upon the results of these experiments, it is apparent that the non-invasive method at the present invention may be sued by biomedical researchers and technologists to identify physiological changes in the body of a pregnant woman in the earliest stages of her pregnancy, and to determine whether the changes are the result of carrying a male or female fetus. Similarly, the marked differences between the patterns of a healthy women and women with cancer indicates that the present invention may also be used to identify pathological changes in a human being. Since the method of the present invention preserves the structural integrity of the DNA complex, the DNA complex tends to aggregate during the deposition phase in an orderly manner, rather than in a random manner. It is this orderly aggregation process that produces the unique patterns.

It should be further understood by those persons who are skilled in the art of biomedical research that the application of the present invention is not limited to its use in diagnosing the gender of a fetus, and in diagnosing breast and cervical cancer. Since the patterns which are used to form the diagnosis are formed from the DNA complex of the blood cells, the existence of all physiological and pathological conditions are potentially detectable using the method of the invention. Although current biomedical technology is not able to completely describe all of the physical changes that take place within the DNA complex of the blood cells when it is exposed to physiological and/or pathological conditions, it is known that changes do occur in the DNA complex of the blood cells in response to such conditions. As a result, the present invention's ability to compare a DNA complex pattern of a the blood cells of a healthy person to the pattern of a DNA complex which has reacted or changed in some manner compels the conclusion that the method may be used to diagnose the existence of all known diseases and to do so at an early stage of the disease.

Although the preferred method of the present invention involves the use of fresh blood as the source material to form the patterns, it will be understood by biomedical researchers that other cellular source materials may also be used to extract the DNA complex and used to form precipitated patterns. Finally, it will also be apparent to those skilled in the art that the method of the present invention, in addition to being applicable to human beings, is equally applicable to all other animals or living cells. Accordingly, the disclosure of the present invention is intended to be illustrative, but not limiting, of the scope of the invention.

We claim:

1. A method of processing human blood samples to form a DNA complex strand pattern, comprising the steps of:
   a. mixing a sample of blood containing plasma and blood cells with an anticoagulant to form an anti-coagulated blood mixture;
   b. centrifuging the anti-coagulated blood mixture in order to separate the plasma from the blood cells;
   c. preparing a first blood cell mixture in accordance with the following steps:
      i. preparing approximately one (1) volume of Tris-buffer;
      ii. adding approximately a half (½) volume of Tris-buffer saturated phenol, prepared by mixing re-distilled phenol with Tris-buffer, to the approximately one (1) volume of Tris-buffer to produce a buffer diluted phenol; and
      iii. adding approximately two (2) volumes of the blood cells to the buffer diluted phenol;
   d. centrifuging the first blood cell mixture to form a first liquid phase and first blood cell debris;
   e. preparing a second blood cell mixture by mixing the centrifuged first blood cell mixture and first blood cell debris with approximately a half (½) volume of chloroform and approximately a half (½) volume of Tris-buffer saturated phenol, prepared by mixing re-distilled phenol with Tris-buffer;
   f. centrifuging the second blood cell mixture to form a second liquid phase and second blood cell debris;
   g. cooling the second liquid phase and second blood cell debris thereby causing the structural components of the DNA complex within the second liquid phase to aggregate;
   h. placing an acid alcohol sample consisting of approximately twelve and a half (12½) volumes of freshly made 20% acid alcohol on a slide; and
   i. adding a blood cell sample consisting of approximately one fifth (⅕) volume of the cooled second liquid phase onto the center of the top surface of the acid alcohol sample and allowing both samples to dry at room temperature without any disturbance, whereby an aggregate of the DNA complex deposits a strand pattern on the slide.

2. A method of processing human blood samples to form a DNA complex strand pattern, comprising the steps of:
   a. mixing a sample of blood containing plasma and blood cells with an anticoagulant to form an anti-coagulated blood mixture;
   b. centrifuging the anti-coagulated blood mixture in order to separate the plasma from the blood cells;
   c. preparing a first blood cell mixture in accordance with the following steps:
      i. preparing approximately 5 ml of Tris-buffer;
      ii. adding approximately 2.5 ml of Tris-buffer saturated phenol, prepared by mixing re-distilled phenol with Tris-buffer, to the approximately 5.0 ml of Tris-buffer to produce a buffer diluted phenol; and
      iii. adding approximately 10 ml of the blood cells to the buffer diluted phenol;
   d. centrifuging the first blood cell mixture to form a first liquid phase and first blood cell debris;
   e. preparing a second blood cell mixture by mixing the centrifuged first blood cell mixture and first blood cell debris with approximately 2.5 ml of chloroform and approximately 2.5 ml of Tris-buffer saturated phenol, prepared by mixing re-distilled phenol with Tris-buffer;
   f. centrifuging the second blood cell mixture to form a second liquid phase and second blood cell debris;
   g. cooling the second liquid phase and second blood cell debris thereby causing the structural components of the DNA complex within the second liquid phase to aggregate;
   h. placing an acid alcohol sample consisting of approximately 25 ml of freshly made 20% acid alcohol on a slide;
   i. adding a blood cell sample consisting of approximately 1.0 ml of the cooled second liquid phase onto the center of the top surface of the acid alcohol sample and allowing both samples to dry at room temperature without any disturbance, whereby an aggregate of the DNA complex deposits a strand pattern on the slide.

3. The method of claim 1 or 2 in which the Tris-buffer consists of 0.5 M Tris, 0.2 M EDTA, 0.6% NaCl, having a pH of between 10.3 and 10.4.

4. The method of claim 1 or 2 in which the step of centrifuging the first blood cell mixture is performed for approximately ten (10) minutes at 11,000 rpm.

5. The method of claim 1 or 2 in which the step of centrifuging the second blood cell mixture is performed for approximately fifteen (15) minutes at 11,000 rpm.

6. The method of claim 1 or 2 in which the step of cooling the second liquid phase is performed by placing the second liquid phase on ice for approximately fifteen (15) minutes.

* * * * *